United States Patent
Hans et al.

(10) Patent No.: US 11,013,714 B2
(45) Date of Patent: May 25, 2021

(54) USE OF HOMOERIODICTYOL (HED) FOR REDUCING THE GASTRIC ACID SECRETION-STIMULATING EFFECT OF N-ACETYL-4-AMINOPHENOL (PARACETAMOL)

(71) Applicant: SYMRISE AG, Holzminden (DE)

(72) Inventors: Joachim Hans, Holzminden (DE); Jakob Peter Ley, Holzminden (DE); Susanne Paetz, Höxter (DE); Silke Middendorf, Bad Laer (DE); Kathrin Liszt, Vienna (AT); Veronika Somoza, Weidling (AT)

(73) Assignee: SYMRISE AG, Holzminden (DE)

( * ) Notice: Subject to any disclaimer, the term of this patent is extended or adjusted under 35 U.S.C. 154(b) by 8 days.

(21) Appl. No.: 16/094,914

(22) PCT Filed: Apr. 19, 2017

(86) PCT No.: PCT/EP2017/059315
§ 371 (c)(1),
(2) Date: Oct. 19, 2018

(87) PCT Pub. No.: WO2017/182538
PCT Pub. Date: Oct. 26, 2017

(65) Prior Publication Data
US 2019/0091199 A1 Mar. 28, 2019

(30) Foreign Application Priority Data
Apr. 20, 2016 (EP) .................................. 16166222

(51) Int. Cl.
*A61K 31/352* (2006.01)
*A61K 31/167* (2006.01)
*A61K 47/22* (2006.01)
*A61K 47/10* (2017.01)
*A61K 9/46* (2006.01)
*A61K 9/20* (2006.01)
*A61K 9/00* (2006.01)
*A61K 9/08* (2006.01)
*A61K 9/16* (2006.01)

(52) U.S. Cl.
CPC .......... *A61K 31/352* (2013.01); *A61K 9/0007* (2013.01); *A61K 9/0056* (2013.01); *A61K 9/0095* (2013.01); *A61K 9/08* (2013.01); *A61K 9/1688* (2013.01); *A61K 9/1694* (2013.01); *A61K 9/2054* (2013.01); *A61K 9/2059* (2013.01); *A61K 31/167* (2013.01); *A61K 47/10* (2013.01); *A61K 47/22* (2013.01)

(58) Field of Classification Search
CPC .. A61K 31/352; A61K 9/0007; A61K 9/0056; A61K 9/0095; A61K 9/08; A61K 9/1688; A61K 9/1694; A61K 9/2054; A61K 9/2059; A61K 31/167; A61K 47/10; A61K 47/22
See application file for complete search history.

(56) References Cited

U.S. PATENT DOCUMENTS 8,685,436 B2 * 4/2014 Ley .................. A23F 3/405
424/439

FOREIGN PATENT DOCUMENTS

| EP | 1258200 A2 | 11/2002 |
| WO | 2014111436 A1 | 7/2014 |
| WO | 2014111546 A1 | 7/2014 |

OTHER PUBLICATIONS

Garcia-Rodriguez et al. Epidemiology Sep. 2001, vol. 12 No. 5 (Year: 2001).*
Bannwarth (2004) Gastrointestinal safety of paracetamol: is there any cause for concern?, Expert Opinion on Drug Safety, 3:4, 269-272, DOI: 10.1517/14740338.3.4.269 (Year: 2004).*
Rainsford and Whitehouse Inflammopharmacology 14 (2006) 150-154 0925-4692/06/040150-5 DOI 10.1007/s10787-006-1389-8 (Year: 2006).*
Walker et al. (Identification of Beer Bitter Acids Regulating Mechanisms of Gastric Acid Secretion, J. Agric. Food Chem. 2012, 60, 6, 1405-1412). (Year: 2012).*
International Search Report and Written Opinion dated Jun. 30, 2017 for corresponding PCT Application No. PCT/EP2017/059315.

* cited by examiner

*Primary Examiner* — Kortney L. Klinkel
*Assistant Examiner* — William Y Lee
(74) *Attorney, Agent, or Firm* — Polsinelli PC

(57) ABSTRACT

The present invention primarily relates to the use of Homoeriodictyol (HED) or a salt thereof or a mixture of HED and one or more salts thereof or a mixture of several salts thereof for reducing the gastric acid secretion-stimulating effect of N-Acetyl-4-aminophenol (Paracetamol).

14 Claims, No Drawings

USE OF HOMOERIODICTYOL (HED) FOR REDUCING THE GASTRIC ACID SECRETION-STIMULATING EFFECT OF N-ACETYL-4-AMINOPHENOL (PARACETAMOL)

CROSS-REFERENCE TO RELATED APPLICATIONS

This application is a national stage application (under 35 U.S.C. § 371) of PCT/EP2017/059315, filed Apr. 19, 2017, which claims benefit of European Application No. 16166222.6, filed Apr. 20, 2016, which are incorporated herein by reference in their entireties.

The present invention relates on the one side to the non-therapeutic use of Homoeriodictyol (HED) for reducing the gastric acid secretion-stimulating effect of N-acetyl-4-aminophenol (Paracetamol) and on the other side to HED or a salt thereof or a mixture of HED and one or more salts thereof or a mixture of several salts thereof for use in a therapeutic method for reducing the gastric acid secretion-stimulating effect or Paracetamol.

Further so-called preferred aspects of the present invention result from the subsequent description including the examples as well as particularly the patent claims.

Paracetamol (N-acetyl-4-aminophenol; N-acetyl-p-aminophenol; 4-Acetaminophenol; Acetaminophen (USAN); APAP; 4'-Hydroxyacetanilide; p-Hydroxyacetanilide; IUPAC: N-(4-Hydroxyphenyl)acetamide; Latin: Paracetamolum; med. Abbreviation: PCM) is an analgesic and antipyretic drug substance of the group of non-opioid analgesics and is diversely used. Paracetamol has, however, a characteristic, slightly bitter taste, which may be perceived as unpleasant. Additionally, Paracetamol may cause reflux-syndromes by stimulating the secretion of gastric acid.

The stimulation of gastric acid secretion generally is an important mechanism for initiating the digestion of food, particularly food rich in proteins. It can indeed be positive for the digestion to additionally stimulate the secretion for a short-term and moderately. If gastric acid is, however, secreted excessively and thus the pH in the stomach is reduced too much, it usually and acutely results in e.g. discomfort or sour belching. If this condition persists for longer time or in case, the gastric acid secretion is chronically stimulated to a high extent, inflammatory conditions of the gastric mucosa as well as the oesophagus may be induced, which in turn can lead to ulcers and in the worst case also malign tissue changes up to gastric cancer or oesophageal cancer.

Object of the present invention was thus to present substances, preferably natural substances, which are suited for reducing the gastric acid secretion-stimulating effect of Paracetamol. Preferably, substances shall be presented, which can particularly strongly reduce or even completely prevent the secretion of acid.

Conventionally, two big groups of substances for reducing the gastric acid secretion or, respectively, for counteracting it are used, namely for one, (neutralizing) basic substances, such as e.g. sodium hydrogen carbonate, calcium carbonate, basic aluminium or magnesium hydroxides, which increase the pH value, and for the other, substances reducing the gastric acid secretion by direct blocking of the acetyl choline receptors (M3-type) or more frequently H2-histamine receptors, both found on the secretory cells (parietal cells), as for example Pirenzepine, Cimetidine, Ranitidine or Famotidine.

A further possibility for reducing the gastric acid secretion is the direct modulation of the ATP-driven proton pump of the parietal cells (as e.g. Opremazol).

Surprisingly, within the scope of the invention it was found that Homoeriodictyol (HED; 3'-Methoxy-4',5,7-trihydroxy flavanone) is capable of not only reducing the bitter taste of Paracetamol, but also for reducing or event completely prevent the gastric acid secretion-stimulating effect of Paracetamol.

The present invention thus relates to the non-therapeutic use of Homoeriodictyol (HED) or a salt thereof or a mixture of HED and one or more salts thereof or a mixture of several salts thereof for reducing the gastric acid secretion-stimulating effect of Paracetamol. Additionally, the present invention also relates to HED or a salt thereof or a mixture of HED and one or more salts thereof or a mixture of several salts thereof for use in a therapeutic method for reducing the gastric acid secretion-stimulating effect of Paracetamol.

Regarding the preferred embodiments (as subsequently described herein), what was said regarding the non-therapeutic application also applies in principle for the application with regard to a therapeutic method, in case nothing contrary is described.

Non-therapeutic applications are preferably such, in which a reduction of the gastric acid secretion-stimulation of Paracetamol by Homoeriodictyol (HED) or a salt thereof or a mixture of HED and one or more salts thereof or a mixture of several salts thereof serves for preventing or reducing a discomfort or sour belching which may be caused by the sole application of Paracetamol. This kind of non-therapeutic application is present, if individuals use a mixture of HED and/or one or more salts thereof and Paracetamol or a preparation, comprising HED and/or one or more salts thereof and Paracetamol, only occasionally, i.e. only several times a year and in low dose, as an analgesic or antipyretic drug substance. At such a rare use of a said mixture or preparation, the stimulation of gastric acid secretion effected by Paracetamol alone would be too low for achieving an effect beyond discomfort and sour belching. The use of Homoeriodictyol (HED) or a salt thereof or a mixture of HED and one or more salts thereof or a mixture of several salts for reducing the gastric acid secretion-stimulating effect of Paracetamol is thus a non-therapeutic use in this case.

Applications within the scope of a therapeutic method are preferably such, in which a reduction of the gastric acid secretion-stimulation of Paracetamol by Homoeriodictyol (HED) or a salt thereof or a mixture of HED and one or more salts thereof or a mixture of several salts thereof serves for preventing or reducing the degree of severity of inflammatory conditions of the gastric mucosa and the oesophagus as well as ulcers or malign tissue changes up to stomach cancer and oesophageal cancer which may be caused by the sole application of Paracetamol. This kind of therapeutic application is present, if individuals frequently use, i.e. during a time period of many days a year and in high dose, a mixture of HED and/or one or more salts thereof and Paracetamol or a preparation, comprising HED and/or one or more salts thereof and Paracetamol, as an analgesic or antipyretic drug substance. An example of such a case are patients with chronic pain, which are frequently dependent on the application of an analgesic such as Paracetamol for pain management. The regular application of Paracetamol alone may lead to the pathological changes of the gastric mucosa and the oesophagus as described above. These may, however, be prevented by the application of HED or a salt thereof or a mixture of HED and one or more salts thereof or a mixture of several salts thereof in addition to Paracetamol, or, respectively, their extent and symptoms may be reduced.

A bitter-masking effect of HED is adequately recognized. Further, WO 2014111436 A1 describes that for example HED is capable of reducing the gastric acid secretion-stimulating effect of diverse substances, particularly of caffeine or Theobromine. Further, it is shown in WO 2014111436 A1 that an administration of sole HED, without addition of gastric acid secretion-stimulating substances, has no significant effect on the proton secretion in HGT-1-cells. It is assumed that this effect in presence of gastric acid secretion-stimulating substances arises by the modulation of bitter receptors. It is known in literature (W. Meyerhof et al., Chem. Senses 2010, 35, 157-170) that caffeine may activate several bitter receptors, e.g. TAS2R43. It is known from own experiments that HED has an effect as antagonist of precisely this receptor type.

Nevertheless, it is surprising that HED is particularly well capable of reducing the gastric acid secretion-stimulating effect of Paracetamol. Because HED is also described as an agonist for the receptor type TAS2R39 (W. S. U. Roland et al., J. Agric. Food Chem. 2013, 61, 10454-10466). TAS2R39 is the only known bitter receptor which can be activated by Paracetamol. According to previous knowledge, it was thus not predictable but rather particularly surprising that the combination of a pure TAS2R39 agonist (Paracetamol) and a—among others—compound (HED) also activating TAS2R39 (but inhibiting other bitter receptors) has as such an effect as described herein. As was revealed by own experiments, HED is not only capable of reducing the gastric acid secretion-stimulating effect of Paracetamol but also and surprisingly of effecting a significant reduction in the constitutive acid secretion (compare hereto the results shown in the example section).

A possible explanatory approach for the feature of HED to reduce the gastric acid secretion-stimulating effect of Paracetamol in such an extent could be that HED and Paracetamol competitively bind to the same receptor, the bitter receptor TAS2R39. Roland et al. (PLoS ONE 2015, 10(3), e0118200) have determined important structural features of (iso)flavonoid based agonists and antagonists of the TAS2R39 receptor in their structure based pharmacophore modelling by using the Snooker software. This is interesting, particularly due to the aspect that until now, no crystal structure of any bitter receptor could be obtained. Roland et al. assumed that TAS2R39 antagonists and TAS2R39 agonists bind to the same receptor and thus diminish or revoke the activation of the receptor by the agonists, as they are not capable of activating the receptor by themselves. The result of said study was that antagonists are structurally characterized in that they do not have a carbon-carbon double bond between the atoms 2 and 3 of the subclass of flavanones. This leads to a tetrahedral (angled) conformation at position 2 for antagonists, whereas most of the agonists have a carbon-carbon double bond and thus show a planar structure and can enter the binding pocket of the TAS2R39 receptor more deeply. Additionally, the examined flavanones were only effective as antagonists, if they had a methoxy group at atom 6. The antagonists further had no hydrogen bond donors in their structure, whereas the examined agonists had at least one position with a hydrogen bond donor.

The present results of Roland et al. indicate that HED is structurally a "hybrid molecule" with regard to its agonistic and antagonistic effects at the TAS2R39 receptor. HED does not possess a carbon-carbon double bond between the atoms 2 and 3, i.e. it has an angled structure and can presumably not enter the binding pocket of the receptor very deeply. However, it possesses no methoxy group at position 6 and has three hydroxyl groups for forming hydrogen bonds, which in turn rather favours an agonistic activity at the TAS2R39 receptor.

The presence of three hydroxyl groups in the structure of HED could potentially lead to a competitive binding of HED and Paracetamol to the TAS2R39 receptor and thus by a stronger ability of forming hydrogen bonds to a higher binding affinity towards the TAS2R39 receptor as Paracetamol. Simultaneously, HED may presumably not enter the binding pocket of the receptor as deeply as the planar agonists due to its angled structure and thus it may not cause a strong agonistic effect.

With regard to the description of HED as TAS2R39 agonist in the literature and its structure, which mainly contains elements causing an agonistic effect, the strong reduction of the gastric acid secretion-stimulating effect of Paracetamol by HED is a surprising effect, particularly in the extent as described herein.

In the scope of own experiments, it was shown that the proton secretion in human parietal cells (HGT-1-cells, human gastric tumour cell line) induced by the use of a concentration of 3 mM Paracetamol was reduced by addition of 0.003 or, respectively, 0.03 mM HED and a significant reduction of the constitutive acid secretion can be effected by addition of 0.3 mM HED. I.e. The proton secretion in HGT-1-cells induced by addition of 3 mM Paracetamol can not only reduced or, respectively, revoked by addition of 0.3 mM HED, but rather and surprisingly less acid is secreted by the HGT-1-cells in this case when compared to the control experiment, which is performed without adding active substances to the cells (over-compensation).

Further, it is preferred that the use also comprises a masking of the bitter taste of Paracetamol.

A bitter taste of an orally applied active substance can strongly influence the acceptance of the drug containing the active substance and the compliance of individuals in a negative way. It is thus important to provide substances masking the bitter taste of another substance in mixtures or preparations comprising this bitter substance.

Masking in the scope of the present text is a reduction, i.e. a decrease or a complete suppression. Masking of a bitter taste impression thus means a regular taste impression, particularly with regard to bitter tastes.

Said taste impression can be achieved by different strategies. Traditionally, unpleasant, bitter taste impressions were masked by the addition of flavourings perceived as pleasant. This is, however, a sole covering of the bitter taste impression. A second approach for reducing of completely suppressing the bitter taste of a bitter substance is to prevent the contact of the bitter substance with the bitter receptors, for example by encapsulation, molecular inclusion or complexing. A third strategy for masking is the use of so-called bitter blockers (antagonists). It was for example found for the TAS2R39 receptor that 6-methoxy flavanone can reduce the reaction of the receptor on diverse bitter substances (agonists) (Roland et al., 6-*Methoxyflavanones as Bitter Taste Receptor Blockers for hTAS2R*39, PLoS ONE 2014, 9(4), e94451). 6-methoxy flavanone clearly has, according to Roland et al. (2015), a structure with is related to TAS2R39 receptor antagonists, i.e. it does not possess a carbon-carbon double bond between the atoms 2 and 3 (angled structure), it has a methoxy group at position 6 and no hydrogen bond donor groups.

According to one aspect of the present invention and within the scope of a use according to the invention, HED and Paracetamol are both contained in a preparation. I.e. a use (as described above) is thus preferred in a preparation comprising HED and/or one or more salts thereof and Paracetamol, wherein the amount of HED and/or salt(s) thereof is sufficient to reduce the gastric acid secretion-stimulating effect of Paracetamol and preferably sufficient to mask the bitter taste of Paracetamol.

Suitable preparations are for example such present in a form selected from the group consisting of tables (non-coated as well as coated tablets, single or multiple layered tablets), capsules, lozenges, granules, pellets, solid substance mixtures, dispersions in liquid phases, emulsions, powders, solutions, juices, pastes or other swallowable or chewable preparations, preferably such selected from the group consisting of tablets, capsules, juices, chewing gums or fruit gums.

Further typical active substances, basic substances, excipients and additives can be present in the preparation in an amount of from 0.9 to 99.999999 wt.-%, preferably 10 to 80 wt.-%, related to the total weight of the preparation. Further, the preparations can contain water in an amount of up to 99.999999 wt.-%, preferably 5 to 80 wt.-%, related to the total weight of the preparation.

Preferably, the preparation further comprises one or more components selected from the group consisting of Eriodictyol, Phloretin, Hesperetin, 2,4-Dihydrobenzoic acid-/V-vanillyl amide, 5,7-Dihydroxy-4-(4-hydroxy-phenyl)-chroman-2-one, 5,7-Dihydroxy-4-(4-hydroxy-3-methoxy-phyenyl)-chroman-2-one, 5,7-Dihydroxy-4-(4-pyridyl)-chroman-2-one, 7,3-Dihydroxy-4'-methoxyflavan, Lariciresinol and Matairesinol and their respective (if applicable) stereoisomers (diastereoisomers or enantionmers) as such or present in mixtures.

In the scope of the present invention, HED or a salt thereof or a mixture of HED and one or more salts thereof or a mixture of several salts thereof and Paracetamol can be administered to an individual either simultaneously or together in a preparation or they can be administered in different preparations and with a temporal shift. I.e. HED and/or one or more salt(s) thereof can be administered to an individual before, during or after the administration of Paracetamol. Preferably, HED and/or one or more salt(s) thereof and Paracetamol are administered simultaneously and in the same preparation.

In case of a simultaneous administration of HED and/or one or more salt(s) thereof and Paracetamol to an individual, i.e. a formulation of these components in the same preparation, HED and/or one or more salt(s) thereof and Paracetamol can be present in mixed form (e.g. in a single layered table) or they can be present in separated layers (e.g. in a two or multiple layered tablet). The release of HED and/or one or more salt(s) thereof and of Paracetamol can occur in two or multiple layered tablets (or other formulation forms) simultaneously or with a time shift after oral administration. Preferably, the release of HED and/or one or more salt(s) thereof occurs before the release of Paracetamol or simultaneously with the release of Paracetamol.

In the scope of the present results of own experiments on the effect of HED (see example section), it is particularly preferred in the scope of the present invention, if the gastric acid secretion-stimulating effect of Paracetamol in the composition is reduced by at least 10%, preferably at least 20%, further preferably at least 50%, particularly preferably at least 70%, especially preferably completely by HED and/or the salt(s) thereof compared to an identical composition without HED and/or salt(s) thereof.

In a particularly preferred embodiment, not only the gastric acid secretion-stimulating effect of Paracetamol is strongly reduced by HED and/or the salt(s) thereof, but also the constitutive acid secretion of the HGT-1-cells (over-compensation) is significantly diminished, i.e. in the scope of the cell assay described in the example section (compare table 1), the level of acid secretion in the HGT-1-cells is lower after the administration of Paracetamol and HED and/or one or more salt(s) thereof as in an untreated control, which was neither contacted with Paracetamol nor HED. In this case, the gastric acid secretion-stimulating effect of Paracetamol in the composition is reduced by HED and/or the salt(s) thereof by at least 150%, particularly preferably by at least 200%, especially preferably by at least 300% compared to an identical preparation without HED and/or salt(s) thereof.

Concerning details with regard to the experimental determination of the reduction of the gastric acid secretion-stimulating effect of Paracetamol by HED and/or salt(s) thereof compared to an identical preparation without HED and/or salt(s) thereof, it is referred to the following example section.

Regarding preferred amounts of HED applies that the concentration of HED and/or salt(s) thereof in the preparation (as described above) is in the range of from 0.000001 to 30 mM, preferably of from 0.00001 to 3 mM, further preferably of from 0.0001 to 1 mM, particularly preferably of from 0.001 to 0.4 mM.

Regarding preferred amounts of Paracetamol applies that the concentration of Paracetamol in the preparation is in a range of from 0.001 to 1000 mM, preferably of from 0.01 to 800 mM, further preferably of from 0.1 to 750 mM, particularly preferably of from 1 to 600 mM.

In the scope of a use according to the invention, particularly in a preparation (as described above), it is further preferred if the ratio of the total concentration of HED and/or salt(s) thereof and the total concentration of Paracetamol is in a range of from 1:100000 to 1:1, preferably of from 1:10000 to 1:2, further preferably of from 1:5000, particularly preferably of from 1:2000 to 1:20.

HED or, respectively, salts thereof are present in a large number of plants. The main source is the Eriodictyon ssp., better known as Herba Santa or Yerba Santa, which belong to the Family of Hydrophyllaceae. Methods for providing or, respectively, for isolating HED and salts thereof, but also other possibilities to obtain HED and its salts are meanwhile well known to a person skilled in the art.

As far as in the scope of a use according to the invention one or more salts of HED are used, it applies that the or, respectively, one, more or all salts of HED is/are preferably selected from the group consisting of sodium, potassium, calcium and ammonium salts.

In the context of the present application, also the following methods are described:

A method for reducing the gastric acid secretion-stimulating effect of Paracetamol in an orally consumable pharmaceutical preparation, comprising the step of adding HED or a salt thereof or a mixture of HED and one or more salts thereof or a mixture of several salts thereof to a pharmaceutical preparation comprising Paracetamol, in an amount sufficient for reducing the gastric acid secretion-stimulating effect of Paracetamol and, preferably, is additionally sufficient for masking the bitter taste of Paracetamol.

Regarding preferred indications of amounts or, respectively, concentrations of HED and/or one or more salt(s) thereof and of Paracetamol, regarding rations of amounts or, respectively, concentrations of these to each other and to further optionally present components in the preparation, it applies what was said above.

Furthermore, a method for reducing the gastric acid secretion in an individual to which Paracetamol is applied is described, comprising the step of administering HED or a salt thereof or a mixture of HED and one or more salt(s) thereof or a mixture of several salts thereof in an amount sufficient for reducing the gastric acid secretion-stimulating effect of Paracetamol and, preferably, also sufficient for masking the bitter taste of Paracetamol, before, after or simultaneously with Paracetamol.

Subsequently the present invention is further described by means of selected examples.

EXAMPLES

Investigations of the Effect of HED
Cellular Model

Human parietal cells (human gastric tumour cell line, HGT-1) were used as cellular model. These were provided by Dr. C. Laboisse (Laboratory of Pathological Anatomy, Nantes, France). The cells are cultured at standard conditions at 37° C., 5% $CO_2$ in DMEM (Dulbecco's Modified Eagel's Medium) with 4 g/L glucose, 10% FBS, 2% L-glutamine and 1% Penicillin/Streptomycin. For measuring the intracellular proton concentration, the cells are treated with Trypsin/EDTA, the cellular viability was determined with Trypan blue staining and 100 000 cells/well were seeded in black 96-well plates.

Determination of the Intracellular pH Value in HGT-1 Cell Cultures

For measuring the intracellular pH value in HGT-1 cell cultures, the dye 1,5-carboxy-seminaphtarhodafluor-acetoxymethyl ester (SNARF-1-AM) was used. The cells in the 96-well plates are washed once with Krebs-Hepes-buffer (KRHP) and incubated with the dye in a concentration of 3 μM dissolved in KRHP for 30 min at 37° C. and 5% $CO_2$. Afterwards, the cells are washed twice with KRHP and substances stimulating gastric acid secretion, as for example 3 mM caffeine, 0.3 mM Theobromine or 3 mM Paracetamol alone or in combination with substances for reducing the gastric acid stimulating effect of the above substances, for example Homoeriodictyol (HED), in various concentrations in phenol red free DMEM in a volume of 100 μL were added; as a further control, the substances stimulating gastric acid secretion as named above were tested alone. Homoeriodictyol is dissolved in double distilled water. The final concentration of solvent, which is added to the cells, is at most 1%. The fluorescent dye is excited at the wave length of 488 nm and the emission is measured at 580 nm and 640 nm. The ratio of the fluorescence values of 580 nm and 640 nm is plotted in comparison to the calibration curve, wherefrom the pH value can be then obtained. For the calibration curve, the cells are treated with a potassium buffer in different pH values of from 7.2 to 8.2 and 2 μM Nigericin. Nigericin equilibrates the intracellular and extracellular pH value so that the intracellular pH value can be defined. The intracellular $H^+$-concentration is obtained from the intracellular pH value. The intracellular proton index (IPX) is calculated by log 2 transformation of the ratio of treated cells and untreated cells (control) (Rubach, M.; Lang, R.; Seebach, E.; Somoza, M. M.; Hofmann, T.; Somoza, V., Mol Nutr Food Res 2012, 56, 325-335; Rubach, M.; Lang, R.; Hofmann, T.; Somoza, V., Ann N Y Acad Sci 2008, 1126, 310-4; Rubach, M.; Lang, R.; Skupin, C.; Hofmann, T.; Somoza, V., J Agric Food Chem 2010, 58, 4153-61; Weiss, C.; Rubach, M.; Lang, R.; Seebach, E.; Blumberg, S.; Frank, O.; Hofmann, T.; Somoza, V., J Agric Food Chem 2010, 58, 1976-85; Liszt, K. I.; Walker, J.; Somoza, V., J Agric Food Chem 2012, 60, 7022-7030; Walker, J.; Hell, J.; Liszt, K. I.; Dresel, M.; Pignitter, M.; Hofmann, T.; Somoza, V., J Agric Food Chem 2012, 60, 1405-12).

The number of indicated replicates relates to technical replicates (tr) or the number of total replicates (n), which results from the number of technical replicates multiplied with the number of biological replicates.

The following table 1 shows the measured percentage increase (positive values) or, respectively, percentage decrease (negative values) of the proton secretion in HGT-1-cells after 10 minutes stimulation by 3 mM caffeine, 0.3 mM Theobromine or 3 mM Paracetamol alone or in combination with Homoeriodictyol (HED) in varying concentrations. The data is displayed as mean and mean standard deviation, n=3-5, tr=6. Statistics: one-way Anova with Holm-Sidak post-hoc test. Significant differences ($p<0.05$) are indicated by letters.

TABLE 1

Influence of the Paracetamol-induced proton secretion of HGT-1 cells by HED compared to the influence of the Theobromine- and caffeine-induced proton secretion (as described in WO 2014111436 A1):

|  | Caffeine 3 mM | | Theobromine 0.3 mM | | Paracetamol 3 mM | |
| --- | --- | --- | --- | --- | --- | --- |
|  | mean | SEM | mean | SEM | Mean | SEM |
| DMEM | 54.80 | 5.61 | 20.92 | 3.37 | 24.10 | 2.23 |
| +0.003 mM HED |  |  | 21.56 | 2.33 | 10.96 | 5.12 |
| +0.03 mM HED | 38.00 | 6.70 | 13.79 | 3.50 | 6.57 | 4.23 |
| +0.3 mM HED | 20.20 | 5.99 | −16.92 | 3.27 | −46.24 | 3.41 |

As table 1 shows, an increase of the proton secretion of 55% is obtained in case the proton secretion of HGT-1 cells is stimulated by 3 mM caffeine, the addition of HED slightly dampens the caffeine-induced increase of the proton secretion, i.e. at simultaneous incubation of the cells with 3 mM caffeine and 0.03 mM HED, the proton secretion is only increased by 38%, whereas at simultaneous incubation of the cells with 3 mM caffeine and 0.3 mM HED, the proton secretion is only increased by 20%.

In case of a stimulation of the proton secretion in HGT-1 cells by 0.3 mM Theobromine alone, an increase in the proton secretion of 21% arises. The addition of HED slightly dampens the Theobromine-induced increase of the proton secretion, i.e. at simultaneous incubation of the cells with 0.3 mM Theobromine and 0.03 mM HED, the proton secretion is only increased by 14%. At simultaneous incubation of the cells with 0.3 mM Theobromine and 0.3 mM HED, the proton secretion is even decreased by 17%.

In case of a stimulation of the proton secretion in HGT-1 cells by 3 mM Paracetamol alone, the proton secretion is increased by 24%. The addition of HED clearly dampens the increase of the proton secretion after addition of Paracetamol. At simultaneous incubation of the cells with 0.3 mM Paracetamol and only 0.003 mM HED, the proton secretion is only increased by 11%. At simultaneous incubation of the cells with 3 mM Paracetamol and 0.03 mM HED, the proton secretion is only increased by 7%. At simultaneous incubation of the cells with 3 mM Paracetamol and 0.3 mM HED, the proton secretion is clearly reduced by 46%.

APPLICATION EXAMPLES

Application Example 1: HED Dosage Forms

HED-1: Homoeriodictyol, purity 95% (company Interquim, Spain)

HED-2: Homoeriodictyol sodium salt variant 1:

10 g Homoeriodictyol (95%) are provided in a flask and 44 g of 3% NaOH-solution are added. The firstly dark brown solution quickly becomes pappy, is then diluted with water until a homogenous suspension and stirred for 1 hour and then freeze dried or spray dried. Yield: 10.44 g; HPLC: 94.2% HED-Na against standard.

HED-3: Homoeriodictyol sodium salt variant 2:

10 g Homoeriodictyol (95%) are suspended in 100 ml ethyl acetate and 44 g of 3% Na—OH solution is added. The firstly clear solution becomes cloudy and the product precipitates. After 1 hour of stirring at room temperature, the suspension is filtered via a pressure ratched and the filter residue is dried in a vacuum drying chamber. Yield: 9.63 g; HPLC 98.5% HED-Na against standard.

HED-4: Homoeriodictyol sodium salt, natural, prepared according to WO 2004/041804.

HED-5: 60.8 wt.-% water are provided and 6.1 wt.-% gum Arabic and 24.3 wt.-% maltodextrin (of maize starch) are dissolved. 8.8 wt.-% of the Homoeriodictyol sodium salt (HED-2, HED-3 or HED-4) are added and mixed with an ultraturrax or another homogenizer. The emulsified suspension is then spray dried in a spray tower (inlet temperature 185-195° C., outlet temperature 70-75° C.) and a spray product loaded with 18-22% of Homoeriodictyol is obtained.

HED-6: 2.5 wt.-% Homoeriodictyol (HED-1) are dissolved in 1,2-propylene glycol.

HED-7: 1 wt.-% of Homoeriodictyol sodium salt (HED-2, HED-3 or HED-4) are dissolved in ethanol.

In the following applications, only ingredients in pharma quality are used.

Application Example 2: Sachets 3.00 g water free citric acid
2.50 g Aspartame
1.00 g ascorbic acid
82.00 g sucrose
10.00 g Paracetamol powder
1.50 g HED-5 (spray dried HED sodium salt on maltodextrin)

The ingredients are mixed and subsequently packed in portions of 5 g.

Dosage: 5 g of powder are added to 100 mL and are administered.

Application Example 3: Effervescent Tablet 50.00 g Paracetamol
27.00 g sorbitol
5.00 g sodium cyclamate
0.80 g saccharin
5.00 g HED-5 (spray dried HED sodium salt on maltodextrin)
2.00 g 1,2-propylene glycol
The components are mixed and subsequently
100.00 g sodium hydrogen carbonate
136.00 g citric acid
are added. After 2 hours, tablets are pressed thereof (2 g/tablet)

Dosage: 1 tablet is added to 100 ml water and then administered.

Application Example 4: Juice 5 ml of juice contain:
200 mg Paracetamol
20 mg HED-1
Further components: Purified water, sucrose, sodium citrate, tragacanth, citric acid, methyl-4-hydroxy benzoate (E218), propyl-4-hydroxy benzoate (E216).

Application Example 5: Powder for Producing a Solution 1 sachet (6 g) contains:
600 mg Paracetamol
80 mg HED-2 (Homoeriodictyol sodium salt variant 1)
Further components: Citric acid, sodium citrate, sucrose 3.7 g, saccharin-sodium salt, sodium cyclamate, maize starch, highly disperse silicon dioxide, ascorbic acid, maltodextrin, butyl hydroxy anisole, modified starch, curcumin, orange flavour.

Application Example 6: Effervescent Tablet 1 effervescent tablet contains:
500 mg Paracetamol
100 mg HED-5
Further components: Ascorbic acid, citric acid, lactose 1H2O, macrogol 6000, methyl cellulose, sodium cyclamate, sodium hydrogen carbonate, sodium sulphate, povidone K25, saccharin sodium salt, simeticon, sorbic acid, citrus flavour.

Application Example 7: Juice 1 bottle (100 ml) contains:
4.000 mg Paracetamol, i.e. one dose (5 ml) contains 200 mg Paracetamol. 200 mg HED-3 (Homoeriodictyol sodium salt variant 2)
Further components: sodium metabisulphite (E223), propylene glycol, saccharin sodium salt, sorbitol solution 70% (non-crystallized) (E420), purified water, flavour type cherry.

Application Example 8: Tablets 1 tablet contains:
50 mg Paracetamol
10 mg HED-5
Further components: Maize starch, povidone, talc, croscarmellose sodium, microcrystalline cellulose, magnesium stearate.

Application Example 9: Solution 100 ml solution contain:
4000 mg Paracetamol
8000 mg HED-6 (2.5% solution of HED-1 in 1,2-propylene glycol)
Further components: Glycerol, sodium metabisulphite, citric acid, sodium hydroxide, acesulfame potassium salt, flavour type red fruit, macrogol, saccharine sodium salt, purified water.

Application Example 10: Tablets 1 tablet contains:
500 mg Paracetamol
50 mg HED-3
Further components: Microcrystalline cellulose, maize starch, stearic acid, povidone Application Example 11: Fruit Gum

| Ingredients Indication of quantity in wt.-% | A | B |
| --- | --- | --- |
| Gelatine | 7.6% | 7.6% |
| Paracetamol | 5% | 5% |
| Symrise citrus flavour with dye | 0.8% | 0.8% |
| HED-1 | 0.5% | — |
| HED-5 | — | 2.5% |
| Water | Ad 100% | Ad 100% |

For producing a fruit gum with 200 mg Paracetamol per dose, the ingredients listed in the above recipe are added to a boiled sugar syrup mixture (89° Brix).

The invention claimed is:

1. A method for reducing gastric acid secretion-stimulating effects of paracetamol comprising administering to a patient in need thereof an effective amount of homoeriodictyol and/or salt(s) thereof, and reducing the gastric acid secretion-stimulating effects of the paracetamol, wherein the patient in need thereof is a patient suffering from an inflammatory condition of the gastric mucosa and/or a patient suffering from chronic pain.

2. The method of claim 1, wherein the homoeriodictyol and/or salt(s) thereof is/are administered simultaneously with paracetamol.

3. The method of claim 1, wherein the homoeriodictyol and/or salt(s) thereof is/are administered separately from paracetamol.

4. The method of claim 1, wherein the gastric acid secretion-stimulating effect is reduced by at least 10%, compared to an identical preparation without the HED and/or salt thereof.

5. The method of claim 1, wherein the gastric acid secretion-stimulating effect is reduced by at least 50%, compared to an identical preparation without the HED and/or salt thereof.

6. The method of claim 1, wherein the gastric acid secretion-stimulating effect is reduced by at least 70%, compared to an identical preparation without the HED and/or salt thereof.

7. A method for reducing gastric acid secretion-stimulating effects of paracetamol comprising administering to a patient in need thereof a pharmaceutical preparation comprising paracetamol and homoeriodictyol (HED) and/or salt(s) thereof in an amount sufficient to reduce the gastric acid secretion-stimulating effect of the paracetamol, and reducing the gastric acid secretion-stimulating effects of the paracetamol, wherein the patient in need thereof is a patient suffering from an inflammatory condition of the gastric mucosa and/or a patient suffering from chronic pain.

8. The method of claim 7, wherein the preparation further comprises one or more of eriodictyol, phloretin, hesperetin, 2,4-dihydrobenzoic acid-/V-vanillylamide, 5,7-dihydroxy-4-(4-hydroxy-phenyl)-chroman-2-one, 5,7-dihydroxy-4-(4-hydroxy-3-methoxy-phyenyl)-chroman-2-one, 5,7-dihydroxy-4-(4-pyridyl)-chroman-2-one, 7,3-dihydroxy-4'-methoxyflavan, lariciresinol, and matairesinol; and their respective stereoisomers.

9. The method of claim 7, wherein the preparation comprises one or more salts of HED, wherein the one or more salts are selected from sodium, potassium, calcium, and ammonium salts.

10. The method of claim 7, wherein the preparation comprises homoeriodictyol (HED) and/or salt(s) thereof in an amount sufficient to mask the bitter taste of paracetamol.

11. The method of claim 7, wherein the gastric acid secretion-stimulating effect is reduced by at least 10%, compared to an identical preparation without the HED and/or salt thereof.

12. The method of claim 7, wherein the gastric acid secretion-stimulating effect is reduced by at least 50%, compared to an identical preparation without the HED and/or salt thereof.

13. The method of claim 7, wherein the gastric acid secretion-stimulating effect is reduced by at least 70%, compared to an identical preparation without the HED and/or salt thereof.

14. The method of claim 7, wherein the preparation is a tablet.

* * * * *